US008020503B2

(12) United States Patent
Ekholm et al.

(10) Patent No.: US 8,020,503 B2
(45) Date of Patent: Sep. 20, 2011

(54) AUTOMATED SURGICAL IMPLANT SEWING SYSTEM AND METHOD

(75) Inventors: C. Roger Ekholm, Dana Point, CA (US); Stephen Christopher Geist, San Diego, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1451 days.

(21) Appl. No.: 11/497,150

(22) Filed: Jul. 31, 2006

(65) Prior Publication Data
US 2008/0035038 A1 Feb. 14, 2008

(51) Int. Cl.
D05B 69/20 (2006.01)
A61F 2/24 (2006.01)
(52) U.S. Cl. .............. 112/475.08; 112/475.17; 623/2.41
(58) Field of Classification Search ............ 112/475.01, 112/475.08, 475.17, 470.01–470.18; 600/36; 623/1.1, 1.15, 1.49, 2.1, 2.4–2.42, 910, 922
See application file for complete search history.

(56) References Cited

U.S. PATENT DOCUMENTS

| 3,709,175 | A | * | 1/1973 | Edwards et al. ......... 112/470.14 |
| 3,710,744 | A | | 1/1973 | Goodenough et al. |
| 5,069,151 | A | | 12/1991 | Bellio |
| 5,140,920 | A | | 8/1992 | Bellio et al. |
| 5,199,365 | A | | 4/1993 | Arnold |
| 5,383,417 | A | | 1/1995 | Norrid |
| 5,488,789 | A | * | 2/1996 | Religa et al. ................ 38/102.2 |
| 5,746,145 | A | | 5/1998 | Cox et al. |
| 6,295,940 | B1 | * | 10/2001 | Shonteff ......................... 112/63 |
| 6,401,641 | B1 | * | 6/2002 | Miyano .................... 112/470.05 |
| 6,564,733 | B2 | | 5/2003 | Butzen et al. |
| 6,645,244 | B2 | | 11/2003 | Shu et al. |
| 7,073,456 | B2 | * | 7/2006 | Phillips et al. ........... 112/475.17 |
| 7,185,597 | B1 | * | 3/2007 | Phillips et al. ........... 112/475.04 |
| 7,189,258 | B2 | * | 3/2007 | Johnson et al. .............. 623/2.11 |
| 7,739,971 | B2 | * | 6/2010 | Chambers et al. ....... 112/475.01 |
| 2004/0176839 | A1 | * | 9/2004 | Huynh et al. .................. 623/2.4 |
| 2006/0276889 | A1 | | 12/2006 | Chambers et al. |

FOREIGN PATENT DOCUMENTS

GB 2355728 5/2001
WO WO02/087471 11/2002

OTHER PUBLICATIONS

International Search Report PCT/US2007/072874/ International Filing Date Jul. 5, 2007.

* cited by examiner

*Primary Examiner* — Ismael Izaguirre
(74) *Attorney, Agent, or Firm* — AnneMarie Kaiser, Esq.

(57) ABSTRACT

A system and method for assembling a prosthetic heart valve, including a procedure for sewing fabric around a heart valve support stent. The system includes a support stent handling component that works in conjunction with a sewing machine component. The sewing machine has a bobbin, and the system includes a non-contact sensor to monitor the passage of a needle thread loop over the bobbin. The sensor may be a monitoring laser, and a controlling processor receives information therefrom for 100% real-time inspection of each stitch. The occurrence of an unsuccessful stitch may prompt the processor to repeat the stitch at a slower speed. The automation of the fabric sewing procedure greatly enhances manufacturing throughput and reduces ergonomic strain on workers.

19 Claims, 5 Drawing Sheets

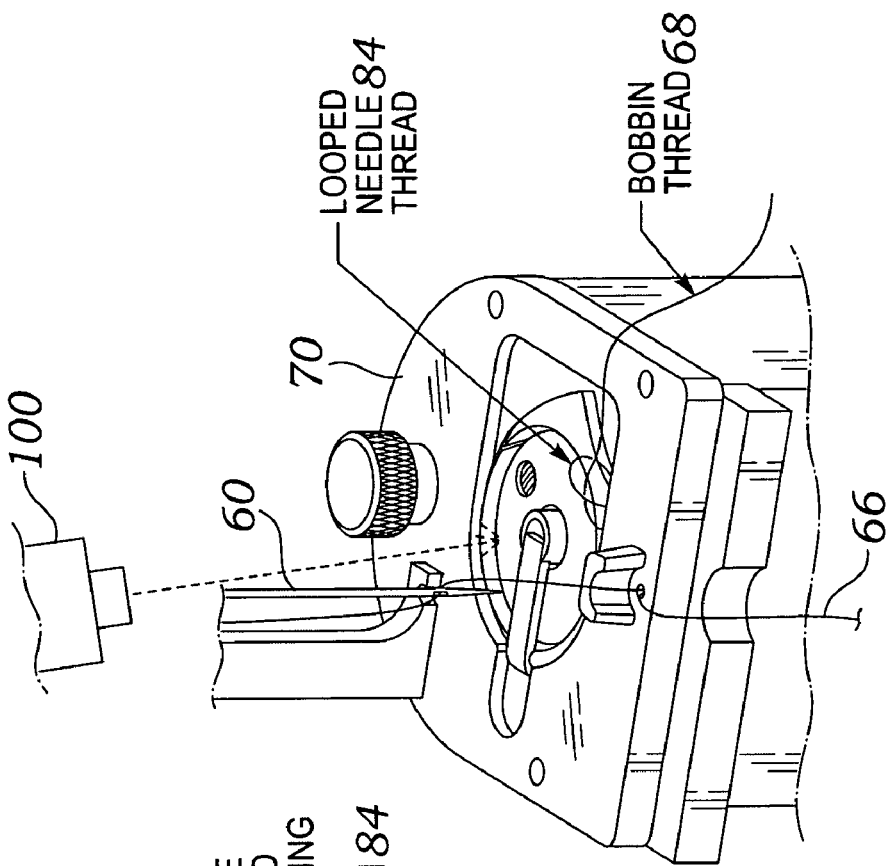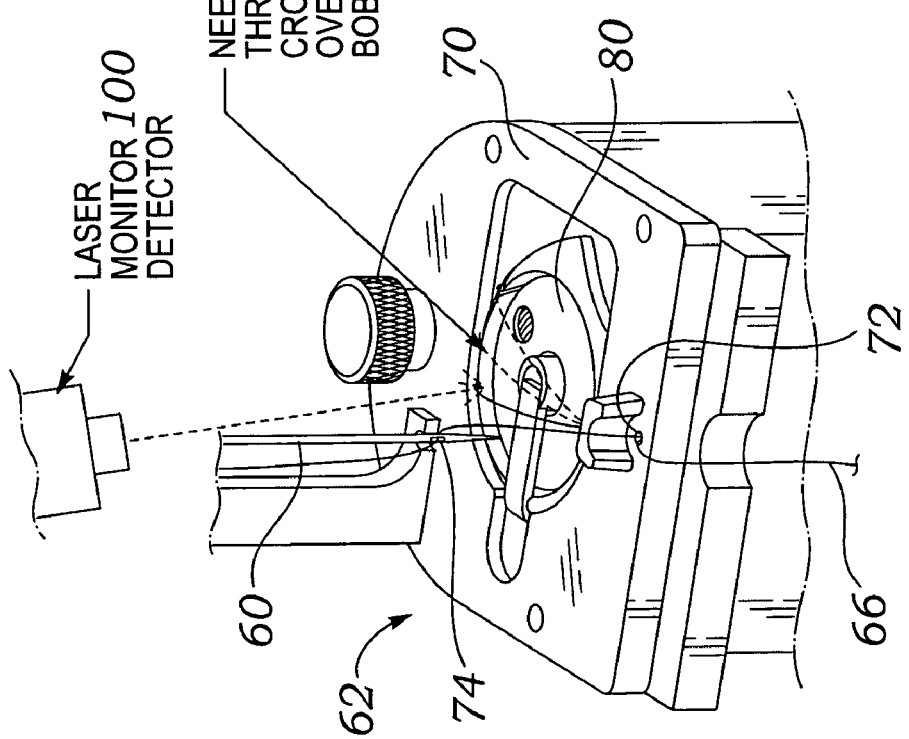

AUTOMATED SURGICAL IMPLANT SEWING SYSTEM AND METHOD

FIELD OF THE INVENTION

The present invention relates generally to medical devices, and more particularly to a system that automates the assembly of components of a fabric-covered prosthetic heart valve, and associated methodology.

BACKGROUND OF THE INVENTION

Heart valve replacement may be indicated when there is a narrowing of the native heart valve, commonly referred to as stenosis, or when the native valve leaks or regurgitates, such as when the leaflets are calcified. In one therapeutic solution, the native valve may be excised and replaced with either a biologic or a mechanical valve. Prosthetic valves attach to the patient's fibrous heart valve annulus, with or without the leaflets being present.

Two primary types of heart valve replacements or prostheses are known. One is a mechanical-type heart valve that uses a ball and cage arrangement or a pivoting mechanical closure supported by a base structure to provide unidirectional blood flow, such as shown in U.S. Pat. No. 6,645,244 to Shu, et al. The other is a tissue-type or "bioprosthetic" valve having flexible leaflets supported by a base structure and projecting into the flow stream that function much like those of a natural human heart valve and imitate their natural action to coapt against each other and ensure one-way blood flow. In tissue-type valves, a whole xenograft valve (e.g., porcine) with leaflets or a plurality of individual xenograft leaflets (e.g., bovine pericardium) provide the fluid occluding surfaces. Synthetic leaflets have been proposed, and thus the term "flexible leaflet valve" refers to both natural and artificial "tissue-type" valves. Two or more flexible leaflets are mounted within a peripheral support structure that usually includes posts or commissures extending in the outflow direction to mimic natural fibrous commissures in the native annulus. For example, the CARPENTIER-EDWARDS Porcine Heart Valve and PERIMOUNT Pericardial Heart Valve available from Edwards Lifesciences of Irvine, Calif. each include a peripheral support structure with an undulating wireform and surrounding stent.

Certain support components of prosthetic valves are assembled with one or more biocompatible fabric (e.g., Dacron, polyethylene terepthalate) coverings, and a fabric-covered sewing ring is typically provided on the inflow end of the valve. The fabric coverings provide anchoring surfaces for sutures to hold the flexible leaflets and sewing ring to the peripheral support structure. In a typical assembly procedure, a technician manually holds a tubular fabric around the support component, and the sewing occurs in two stages; first, intermittent stitches are placed to secure the fabric in its gross position around the stent, and then a closely-spaced line of stitches is applied to complete the seam, still with some manual tension on the fabric. The holding and stitching operation is entirely manual and done under a magnifier, which makes it quite labor-intensive and time-consuming. The work requires the passage of needle and thread through multiple layers of fabric and sometimes biological tissue, and requires considerable effort and precision. Needless to say, repetitive stress injuries can occur which is painful to the worker and indirectly increases the cost of making the valve. The number one factor for injury and lost time in this field is the intricacy of manual sewing.

Rigorous quality control in the manufacture of heart valves further increases the difficulty of the task because the fabric must be tightly fitted around the support component and every stitch carefully placed for consistency. Operator-to-operator variability in sewing technique, stitch tension, stitch pitch, and other variables can result in subtly different construction and end product quality. A typical tissue-based heart valve requires 6-8 hours of manual construction, and the manual sewing procedure represents a substantial portion of the cost of the entire valve fabrication process. Moreover, training of heart valve assembly operators to become proficient in sewing can take upwards of 12-14 months.

Automation is usually an option in manufacturing processes, but is not a factor in the production of prosthetic heart valves because of their odd shapes and strict quality control. Indeed, manual sewing has the advantage of the operator being able to continually check the quality and success of their sewing. Mistakes can be corrected on the spot. Although automation speeds the process up, and is quite repeatable and reliable, it is not infallible and the careful manual visual inspection of each stitch would be lost. In general, because most of the steps in assembling prosthetic heart valves are specialized tasks performed in a clean room to produce an implant that must be highly sterile and perfectly assembled, robotics and other such ubiquitous tools of automation are not easily adapted.

There is thus a need for an improved method for assembling flexible heart valves that reduces the assembly time and the instances of injury to the assembly-line workers.

SUMMARY OF THE INVENTION

In accordance with one aspect of the present invention, an automated system is provided for assembling components of a prosthetic heart valve having a fabric-covered support structure defining a central axis. The system comprises a sewing machine including a needle and bobbin for forming a seam with thread in fabric, the sewing machine having components that satisfy FDA class III device manufacturing requirements. A mount holds and rotates a support structure of the prosthetic heart valve about its axis in conjunction with movement of the sewing machine needle during formation of the seam. A sensor detects the presence of thread over the bobbin on each successful stitch, and a processor receives input from the sensor and controls the movements of the sewing machine and clamp based upon said input.

Desirably, the components of the sewing machine that satisfy FDA class III device manufacturing requirements include medical and food grade bearing lubricants materials, and/or at least one factory sealed servo- or stepper-type motor. The support structure of the prosthetic heart valve may be an annular stent and the mount has separable parts for receiving and clamping the fabric over the stent during formation of the seam. Preferably, the sensor comprises a monitoring laser. An air jet may be positioned adjacent the sewing machine needle and directed to form a loop in the thread and facilitate its capture by a bobbin hook. In one embodiment, the sewing machine has at least two speeds, and the processor includes instructions to repeat a stitch at a slower speed on condition of an unsuccessful stitch.

Another aspect of the invention is an automated method for assembling components of a prosthetic implant having a fabric-covered support structure defining a central axis. The method comprises establishing a clean room that satisfies FDA class III device manufacturing requirements, and within the clean room providing a prosthetic implant support structure and a fabric for covering the support structure. The support structure with the fabric thereover is secured on a mount that is rotated adjacent a needle of the sewing machine. A circular seam is formed by the sewing machine with a plurality of thread stitches in the fabric. The success of each thread stitch is monitored and the sewing process modified on the occurrence of an unsuccessful thread stitch.

Desirably, the support structure comprises a stent for a prosthetic heart valve, and may further include a sewing ring wherein the fabric covers both the sewing ring and stent. The mount may have separable components, wherein the method includes clamping the fabric tautly around the support structure with the separable components of the mount. Preferably, the step of monitoring comprises using a non-contact sensor. For example, the non-contact sensor is a monitoring laser, and the sewing machine comprises a bobbin, the monitoring laser being directed toward the bobbin to monitor the passage of a needle thread thereover. The step of modifying may involve repeating an unsuccessful stitch at a slower speed. A flow of air may be directed toward the needle of the sewing machine to form a loop in the thread and facilitate its capture by a bobbin hook.

In accordance with another aspect of the present invention, a method of increasing yield in the fabrication of prosthetic heart valves comprises automatically forming a thread seam in fabric surrounding a support structure of the prosthetic heart valve, the seam comprising a plurality of individual stitches, and automatically monitoring the successful completion of each stitch in the seam prior to formation of another stitch. The support structure may comprise an annular stent and sewing ring, and the fabric covers both the sewing ring and the stent. The method is preferably performed in a clean room and comprises a sewing machine component which interacts with a workpiece handling component both being built and operated to satisfy FDA class III device manufacturing requirements. The movements of the sewing machine component and workpiece handling component may be controlled by a processor which indexes the prosthetic heart valve support structure prior to every stitch. Desirably, placement of each stitch is accurate to within a tolerance of 0.002 inches (0.051 mm). In one embodiment, the step of automatically monitoring comprises directing a monitoring laser toward a bobbin of the sewing machine to monitor the passage of a needle thread thereover. The method may include repeating an unsuccessful stitch at a slower speed on the occurrence of an unsuccessful stitch.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 2A and 2B are enlarged perspective views of a needle and bobbin subsystem of the system of FIG. 1A illustrating one technique for monitoring the formation of successful stitches;

DETAILED DESCRIPTION OF THE PREFERRED EMBODIMENTS

The present invention provides a system for automating one or more steps of a prosthetic heart valve fabrication procedure. The steps of the procedure illustrated and described involve sewing a tubular piece of fabric around a support structure of the prosthetic heart valve, typically a support stent. It should be understood by those of skill in the art that the illustrated support stent is only exemplary, and the present invention can be used to cover various support stents or structures. Furthermore, various aspects of the present invention may be used in other steps of a heart valve fabrication process. For example, mechanisms similar to those shown and described may be used to cover other parts of a prosthetic heart valve with fabric. Up to now, prosthetic heart valve assembly has been an almost entirely manual, labor-intensive process. The present invention therefore represents a pioneering effort to automate at least some of the process of assembling heart valves.

The present invention involves automatically fastening or sewing fabric over the support stent. Desirably, the sewing step is accomplished with a means for automatically forming a seam in the fabric, such as with a sewing machine needle. The term "sewing machine" is intended to refer to any automated device for forming a seam in fabric using a plurality of thread stitches. Likewise, "thread" refers to a filament suitable for forming continuous stitches in fabric, typically polypropylene thread for surgical implant applications. In the context of the present invention, the term "automated" means that once initiated, a particular assembly procedure, in this case forming a seam, may proceed without further manual assistance. Of course, the presence of system operators who monitor the automated assembly procedure may be required, as well as their involvement during steps such as changing workpieces or thread, or attending to malfunctions. However, these manual tasks are not to be considered as part of the "automated" assembly procedure.

Figure 1A:
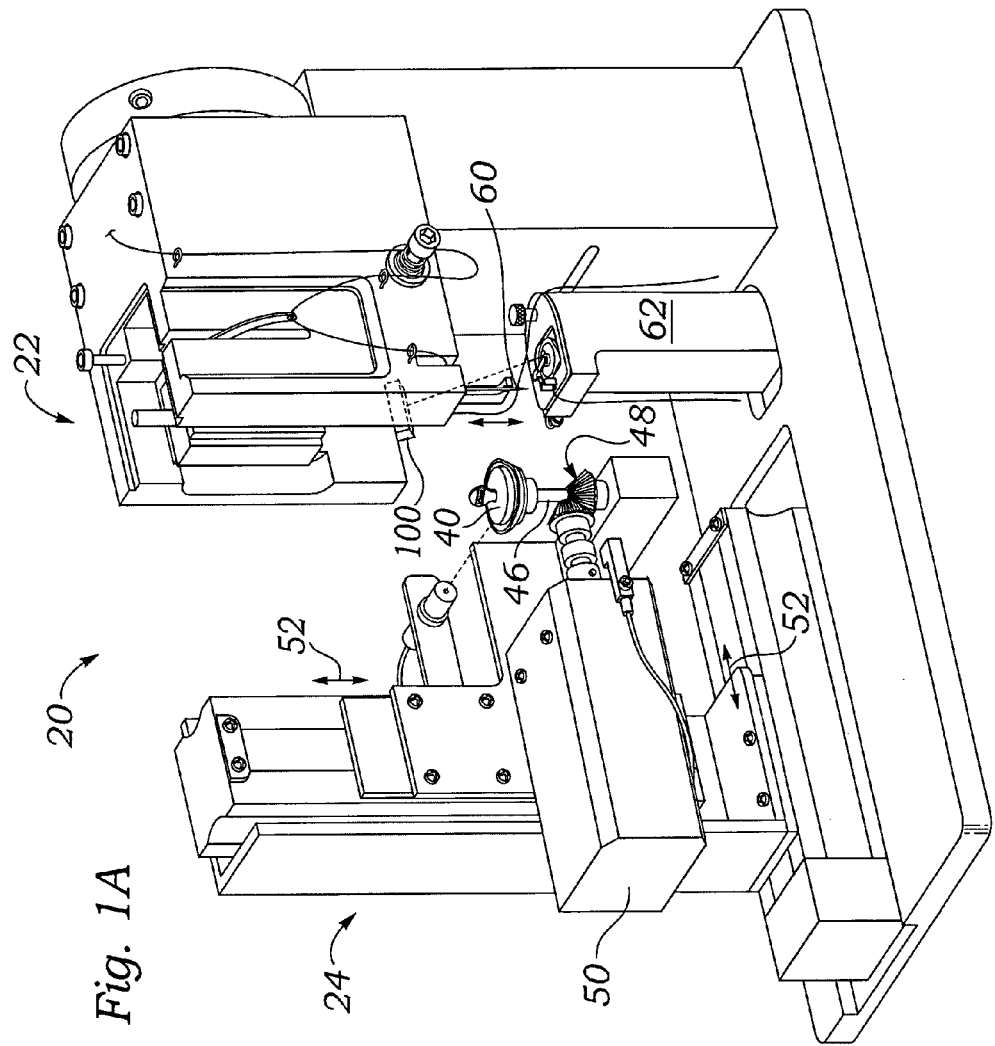
FIG. 1A is a perspective view of an exemplary system for automatically forming a seam in fabric surrounding a prosthetic heart valve support structure, prior to an assembly procedure.
Figure 1B:
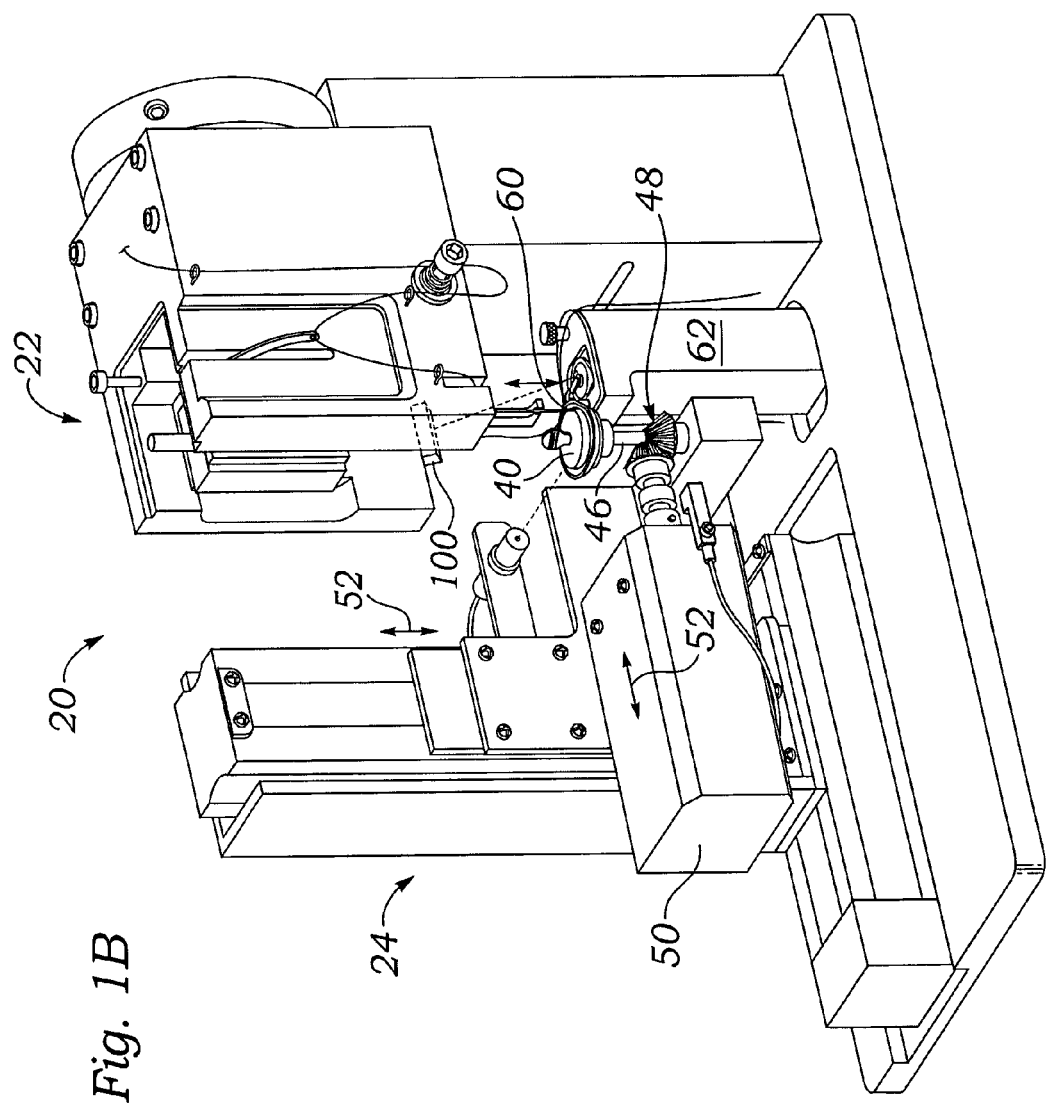
FIG. 1B is a perspective view of the system of FIG. 1A during an automated assembly procedure to form a seam in the fabric surrounding the support structure.

With reference now to FIGS. 1A and 1B, an automated system 20 for forming a seam in fabric is explained. The system 20 generally comprises a sewing machine component 22 which interacts with a workpiece handling component 24. The workpiece in this case is a support structure for a prosthetic heart valve around which a fabric covering will be secured by forming a seam therein using the sewing machine 22. The equipment essentially duplicates the eye-hand coordination and motion of manual sewing. The valve or valve components are held, presented, and indexed via custom designed fixtures and tools that free up the hands of the operator. The operator essentially is tasked with the loading of the parts and the control of the equipment via control panel instructions and motions. Pre-programmed sewing routines or sophisticated pixel-based vision systems replace the eyes of the operators and eliminate eye strain, the need for magnification, and the tedious job of "counting loops" to determine stitch pitch and suture placement.

Figure 3:
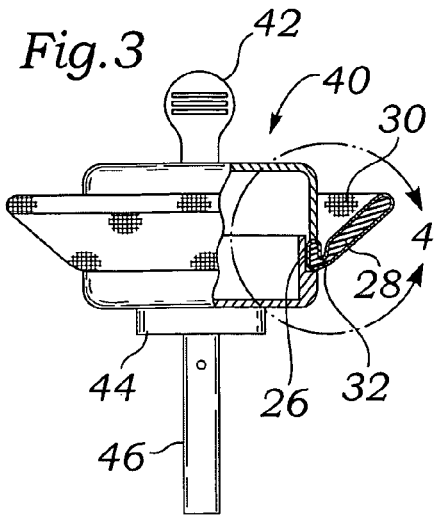
FIG. 3 is a partially cutaway view of an exemplary heart valve support stent and sewing ring covered by fabric and held firmly together on a mount so as to be secured by a seam formed in accordance with the present invention.

As mentioned, various heart valve support structures, and other surgical implant workpieces, may be processed by the system 20. In the exemplary embodiment, as seen better in FIG. 3, the workpiece comprises an annular heart valve support stent 26 secured to an annular suture-permeable sewing ring 28 with a fabric covering 30. In particular, the fabric covering 30 is initially formed as a tube which is draped or wrapped around the support stent 26 and sewing ring 28 and fastened thereover by forming a seam 32 to secure the free ends together. The cross-section indicates that the support stent 26 and sewing ring 28 are the same material, though typically the support stent is metal or rigid plastic while the sewing ring is soft, such as silicone. It will be understood that these elements represent a "support structure" of a prosthetic heart valve, and also represent other implant support structures, such as a metal stent that will be covered with fabric using a seam.

Figure 4:
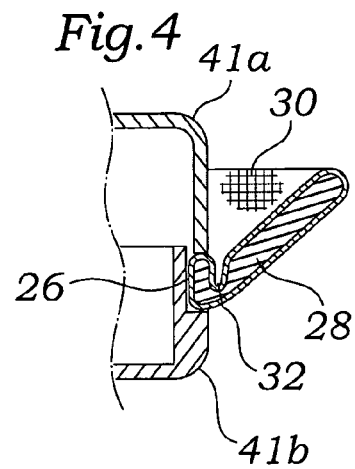
FIG. 4 is an enlarged view of the sectioned edge of the fabric-covered support structure in FIG. 3.

The assembly of the support stent 26, sewing ring 28, and fabric 30, is held on a rotatable mount 40 while forming the seam 32. The mount 40 generally comprises a split cylinder with top and bottom halves 41a, 41b (FIG. 4) for clamping around the support stent 26 using a locking key or thumb screw 42. The top and bottom cylinder halves 41a, 41b hold the fabric 30 tautly around the support stent 36 and sewing ring 28, and represent any number of such mounts or clamps that perform the function of maintaining tension on the fabric during the sewing process. These semi-autonomous mounts eliminate manual stretching of cloth over wireforms, for example, and holding and squeezing of the part for registration and resistance, all of which can cause significant hand, wrist, and shoulder joint trauma. Also, manual handling, squeezing, and manipulation of valve components can result in out-of-specification dimensions and the need for re-work or rejection. An additional benefit of fixtures such as the mount 40 is that they induce minimal stress or component deflection to the sewn parts and therefore result in a more consistent post-sewn component.

With reference again to FIGS. 1A and 1B, the mount 40 rests on a pedestal 44 which, in turn, rotates about the shaft 46 via a pair of bevel gears 48 journaled at 90° to one another. The bevel gears 48 rotate on a housing 50 capable of vertical movement and horizontal movement toward and away from the sewing machine 22, as indicated by arrows 52. The mechanisms and systems for translating and rotating the workpiece mount 40 are conventional, such as servo motors controlled by a programmed linear controller (PLC), and will not be described further herein. Suffice it to say that the edge of the workpiece can be brought into proximity with a needle 60 of the sewing machine 22 and thereupon rotated to form the continuous circular seam 32.

Figure 5:
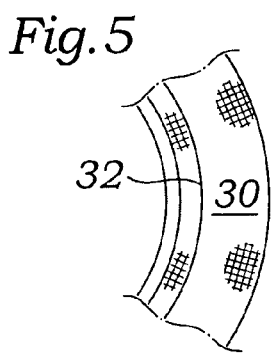
FIG. 5 is a partial top view of an edge of a fabric-covered support structure illustrating a circular seam formed therein.
Figure 6:
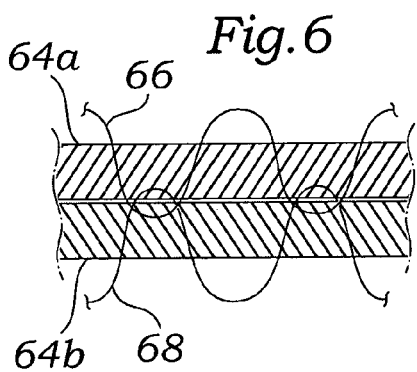
FIG. 6 is a sectional view through two layers of fabric showing a typical series of stitches used to form the seam of FIG. 5.
Figure 7:
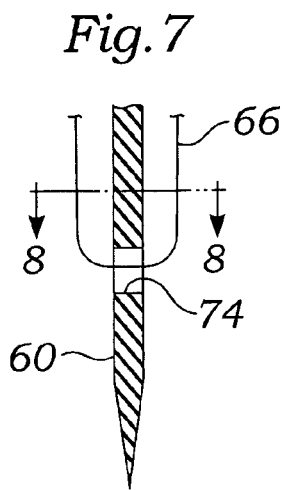
FIG. 7 is an axial sectional view through a needle carrying a thread used to form a stitch.

The sewing machine 22 comprises mechanisms and systems for reciprocating the needle 60 relative to a bobbin platform 62, also seen in detail in FIGS. 2A and 2B. There are a number of different automated stitches that may be performed by the sewing machine 22, including a basic chain stitch and a lock stitch. To ensure integrity of the heart valve, a 301 lock stitch is preferred. FIG. 6 illustrates several lock stitches joining two layers of fabric 64a, 64b. Namely, a thread 66 carried by the needle 60 on one side of the layers loops around a segment of another thread 68 that is carried by a bobbin (described below) on the other side. Repetitive cycles of this looping operation at evenly-spaced locations around the fabric tube 30 creates the circular lock-stitch seam 32 (FIG. 5). For further explanation of a lock-stitch and other seams the reader should refer to the web site http://home.howstuffworks.com/sewing-machine2.htm.

The workpiece mount 40 may be programmed to incrementally rotate the workpiece and form stitches of different pitches. Desirably, the pitch of the stitches remains constant for different sized prosthetic heart valve support stents, even though the stents are of different diameters and fit on different sized mounts 40. An average stent requires sixty stitches to complete a full seam 32, less for the smallest stents and more for the largest. The software and drive mechanisms of the system 20 are desirably accurate enough to place stitches within a tolerance of 0.002 inches (0.051 mm), which is well beyond the capability of a manual operation. Additionally, stitch tension is controlled and monitored with specific ranges using tight bands (not shown), whereas there is considerable variation from operator to operator in prior manual methods.

FIGS. 2A and 2B best illustrates an exemplary system for ensuring continuity of the stitch sequence in the seam 32. A bobbin platform 62 includes a sewing table 70 that defines a small aperture 72 for receiving the reciprocating needle 60. The needle thread 66 passes through an eye 74 in the needle 60 and is thereby carried through the aperture 72 and below the table 70. A bobbin assembly 80 mounts for rotation in a space under the table 70, and in proximity with the lower end of the aperture 72. The bobbin assembly 80 carries the bobbin thread 68 which pays out as needed.

As customary with such rotating bobbin assemblies 80, a hook 82 (FIG. 8) captures a loop 84 formed by the needle thread 66 and carries it around the bobbin assembly 80 to form the lockstitch. Passage of the needle thread loop 84 over the bobbin assembly 80 is seen in stages in FIG. 2A, and after having gone completely around the bobbin assembly in FIG. 2B. Each time the needle thread loop 84 passes over the bobbin assembly 80, it captures a segment of the bobbin thread 68 which forms one stitch of the seam 32.

Figure 8:
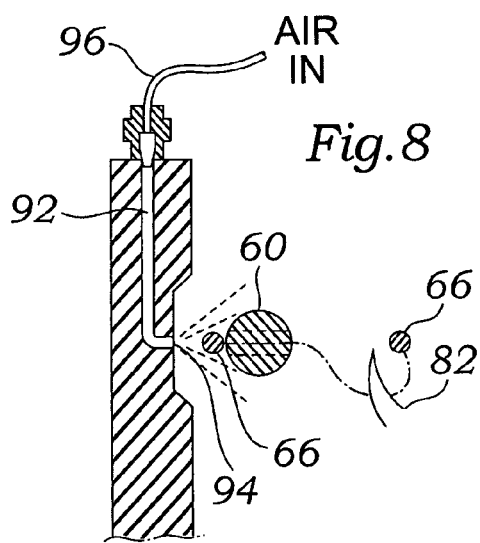
FIG. 8 is a sectional view through the needle taken along line 8-8 of FIG. 7, and an adjacent air jet subsystem.

The small diameter and material characteristics of the needle thread 66 sometimes impede the formation of an initial small loop that can be snagged by the hook 82. FIG. 8 illustrates an exemplary technique for ensuring formation of this initial loop, and thus reducing the possibility of a missed stitch. Specifically, a manifold 90 defines an air passage 92 within that opens at a nozzle 94. The nozzle 94 points directly toward the sewing needle 60 just below the sewing table 70. A conduit 96 supplies compressed air which is forced out of the nozzle 94 and causes the needle thread 66 on the right side to bend to the right, much like a flag waving in the wind, ensuring that the bobbin hook 82 snags it. The needle thread 60 on the left side is maintained in greater tension and is thus not carried into the path of the hook 82.

The automated system 20 of FIG. 1A further includes a monitoring subsystem including a sensor 100 mounted above the bobbin platform 62 that provides 100% inspection of stitch completion during the actual sewing (i.e., in "real-time"). As seen better in FIGS. 2A-2B, the sensor 100 monitors a space adjacent the bobbin assembly 80 over which the needle thread loop 84 crosses. The sensor 100 monitors for the presence or passage of the loop 84 to ensure that a proper stitch is formed. If the loop 84 is not present, the sensor 100 alerts the system 20 of the failure. Several different actions by the system 20 are then possible, as will be detailed below.

It should be noted that a missed stitch or series of stitches may be detected and corrected by post sewing visual inspection. Therefore, a "real-time" monitoring system for each stitch may not be necessary. However, there are situations where a missed stitch can result in the need to junk the entire component. Moreover, post-sewing visual inspection of stitch placement and quality is currently commonly used in industry, but is time-consuming and difficult due to the fact that the sutured cloth material and sutures themselves are the same material and identical in terms of color, contrast and texture. Attempting to visually inspect white stitches against a white cloth background is difficult. Ideally, the present system 20 can be validated such that post-sewing visual inspection can be eliminated.

In an exemplary embodiment, the sensor 100 comprises a monitoring laser that directs an optical beam downwards to the edge of the bobbin assembly 80, and an optical receiver to detect the presence of the loop 84. Such monitoring lasers are available from Keyence of Osaka, Japan (world.keyence.com). The receiver is programmed and instructed to look for optical changes in the reflected field of view it is monitoring. For example, the laser beam is aimed to the bobbin assembly 80, or the space adjacent thereto, which results in a known reflected light that can be calibrated into the system. Upon passage of the typically white thread loop 84, the expected transient reflection from the thread is sensed by the optical receiver. Through a controlling programmer, the system 20 receives a signal that a stitch is being initiated and the optical receiver watches for the reflection of the thread loop 84. Failure to sense the presence of the light reflected from the thread loop 84 at the proper time denotes failure of the completed stitch, and the software connected to the sensor 100 is so notified.

A correctly completed stitch can, of course, be detected in several ways, for example using load cells or thread path tension switches. However, the non-contact optical system described above is believed much more robust for the present application which must satisfy the requirements of the United States Food and Drug Administration for class III devices (described below). The monitoring system ideally provides assurance of 100% stitch success which, in turn, potentially leads to the elimination of 100% post-process quality inspection and its associated cost. For example, after a validation period in which every sewn component is inspected, a level of confidence may be attained permitting a reduction of inspection to every other component, or less. Because of the critical importance of stitch perfection, random or periodic reinstitution of 100% inspection of components is advisable to justify the switch to a reduced inspection level.

There are a number of possible outcomes upon a missed stitch. For example, the system 20 may halt so that the operator can determine the cause of the error. Or, the system 20 may not index to the next stitch and attempt to correctly place a stitch again in the same spot it previously missed. The equipment can be programmed to attempt multiple tries and then stop if unsuccessful. During the retries the machine may assume a slower speed to try and optimize sewing conditions and complete the previously missed stitch.

Figure 9:
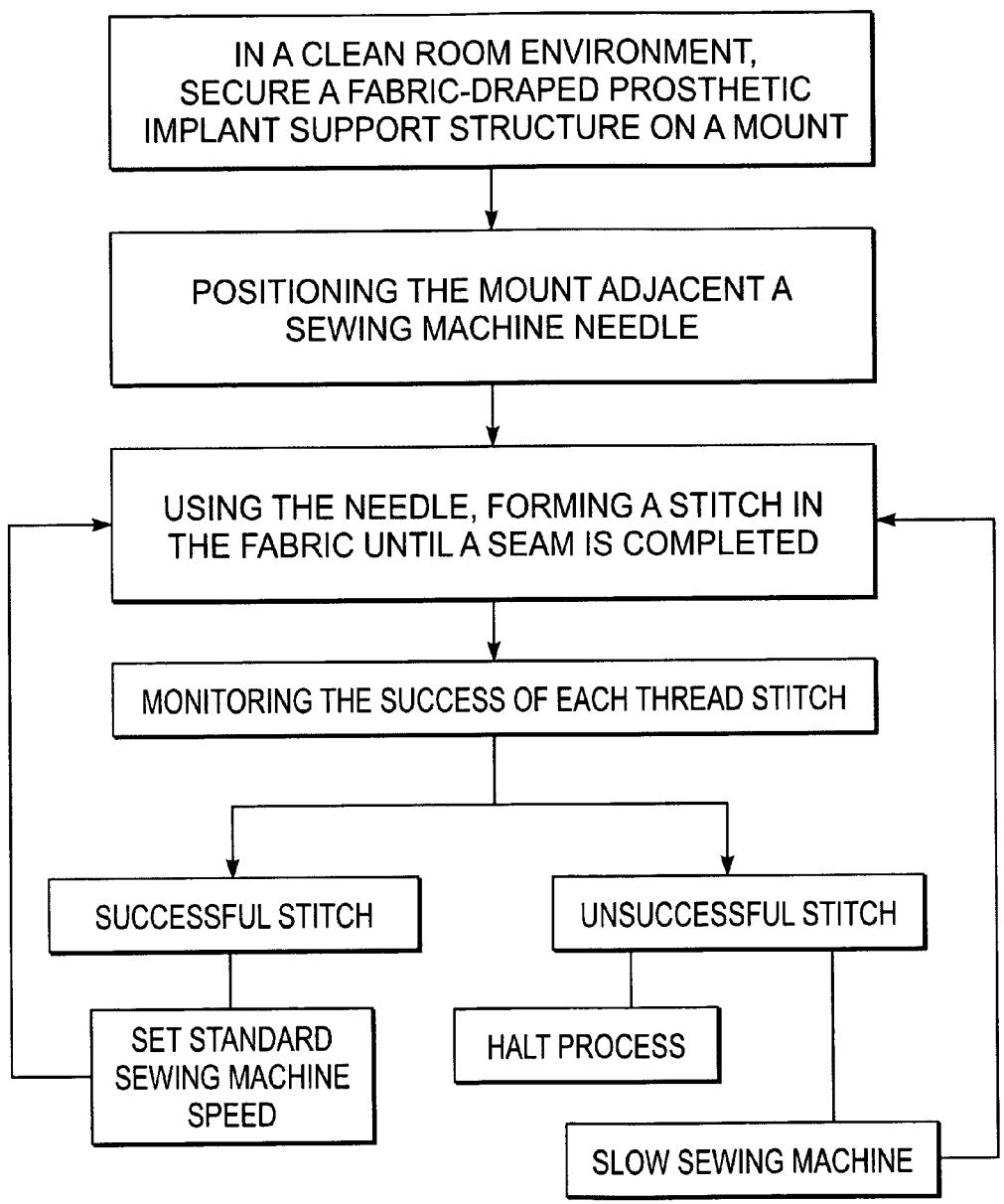
FIG. 9 is a flow chart illustrating several possible outcomes of a stitch monitoring process.

FIG. 9 is a flow chart indicating several possible outcomes of the stitch monitoring process.

Furthermore, the system 20 can be programmed to report on the initial success rate of every sound component. Components that have reports showing increasing levels of initial failures and retry stitches may indicate to the operator that the system requires adjustment or maintenance.

Tests of the system 20 have reduced cycle time for assembling the fabric 30 over the support stent 26 and sewing ring 28 to less than one third of the time for the manual operation (e.g., 18 minutes down to 5). Once completed, the entire automated sewing initiative for conventional tissue heart valves has the potential to reduce sewing cycle time by nearly 50% (with associated direct labor savings). It is estimated that the direct annual labor savings to the present assignee could be in the area of $4 million.

It is important to understand the difference between the present implant fabrication system and existing textile manufacturing systems with which it shares some general aspects (e.g., a reciprocating needle creating a lock stitch). The Medical Device Amendments of 1976 to the Federal Food, Drug, and Cosmetic Act (the act) established three regulatory classes for medical devices. The three classes are based on the degree of control necessary to assure that the various types of devices are safe and effective. The most regulated devices are in Class III, which are defined as those that support or sustain human life or are of substantial importance in preventing impairment of human health or present a potential, unreasonable risk of illness or injury. Under Section 515 of the act, all devices placed into Class III are subject to pre-market approval requirements. Pre-market approval by FDA is the required process of scientific review to ensure the safety and effectiveness of Class III devices.

In the context of a manufacturing facility that produces Class III medical implants, the requirements are numerous and detailed. One of those is that the products be manufactured in a clean environment. Of course, there are various notions of "clean" manufacturing facilities, from those used in food processing all the way up to the ultra-clean conditions within silicone wafer handling rooms. For Class III medical devices, the standards for ensuring that the products remain sterile are relatively stringent. One of those is that any machinery utilized not generate particulate matter which might contaminate the clean room environment.

Consequently, the system 20 has been designed to operate in the absence of particulate matter and contaminants such as grease, oil, and heavy metal contact. Conventional sewing machines are quite dirty in operation due to exposed mechanisms such as cams, followers, belt drives, bearings, etc. To avoid these sources of contamination, the system 20 operates without conventional bearing surfaces by, for example, substituting traditional lubricants with medical and food grade bearing materials. Further, mechanization is limited by replacing cams and levers with factory sealed servo and stepper-type motor technology. Also, conventional machine materials such as case iron, steel, bronze, etc. are replaced with FDA grade stainless steel, anodized aluminum and medical grade plastics such as Delrin and Teflon. Furthermore, to the extent possible, shrouds and seals are provided to physically separate different areas of the system, and as much as possible mechanization is placed below product areas. The aggregate of these efforts produces a system that satisfies FDA Class III device manufacturing requirements, and is accordingly significantly more complex and expensive than conventional sewing machines.

While the invention has been described in its preferred embodiments, it is to be understood that the words which have been used are words of description and not of limitation. Therefore, changes may be made within the appended claims without departing from the true scope of the invention.

What is claimed is:

1. An automated system for assembling components of a prosthetic heart valve having a fabric-covered support structure defining a central axis, the system comprising:

a sewing machine including a needle and bobbin for forming a seam with thread in fabric, the sewing machine having components that satisfy FDA class III device manufacturing requirements;

a mount for holding and rotating a support structure of the prosthetic heart valve about its axis in conjunction with movement of the sewing machine needle during formation of the seam;

a sensor positioned to detect the presence of thread over the bobbin on each successful stitch; and a processor that receives input from the sensor and controls the movements of the sewing machine and mount based upon said input.

2. The system of claim 1, wherein the components of the sewing machine that satisfy FDA class III device manufacturing requirements are selected from the group consisting of:
medical and food grade bearing lubricants materials; and
at least one factory sealed servo- or stepper-type motor.

3. The system of claim 1, wherein the support structure of the prosthetic heart valve is an annular stent and the mount has separable parts for receiving and clamping the fabric over the stent during formation of the seam.

4. The system of claim 1, wherein the sensor comprises a monitoring laser.

5. The system of claim 1, further including an air jet positioned adjacent the sewing machine needle and directed to form a loop in the thread and facilitate its capture by a bobbin hook.

6. The system of claim 1, wherein the sewing machine has at least two speeds, and the processor includes instructions to repeat a stitch at a slower speed on condition of an unsuccessful stitch.

7. An automated method for assembling components of a prosthetic implant having a fabric-covered support structure defining a central axis, and method comprising:
in a clean room that satisfies FDA class III device manufacturing requirements:
providing a prosthetic implant support structure;
providing a fabric for covering the support structure;
securing the support structure with the fabric thereover on a mount;
rotating the mount adjacent a needle of a sewing machine while forming a circular seam with a plurality of thread stitches in the fabric;
monitoring the success of each thread stitch; and
modifying the sewing process on the occurrence of an unsuccessful thread stitch.

8. The method of claim 7, wherein the support structure comprises a stent and sewing ring for a prosthetic heart valve and the fabric covers both the sewing ring and the stent.

9. The method of claim 7, wherein the mount comprises separable components, and further including clamping the fabric tautly around the support structure with the separable components of the mount.

10. The method of claim 7, wherein the step of monitoring comprises using a non-contact sensor.

11. The method of claim 10, wherein the non-contact sensor comprises a monitoring laser, and the sewing machine comprises a bobbin, the monitoring laser being directed toward the bobbin to monitor the passage of a needle thread thereover.

12. The method of claim 7, wherein the step of modifying comprises repeating an unsuccessful stitch at a slower speed.

13. The method of claim 7, further including directing a flow of air toward the needle of the sewing machine to form a loop in the thread and facilitate its capture by a bobbin hook.

14. A method of increasing yield in the fabrication of prosthetic heart valves having a fabric-covered support structure, said method comprising:
performing the following steps in a clean room that comprises a sewing machine component which interacts with a workpiece handling component, both being built and operated to satisfy FDA class III device manufacturing requirements:
(a) automatically forming a thread seam in the fabric surrounding the support structure of the prosthetic heart valve, the seam comprising a plurality of individual stitches; and
(b) automatically monitoring the successful completion of each stitch in the seam prior to formation of another stitch.

15. The method of claim 14, wherein the support structure comprises an annular stent and sewing ring, and the fabric covers both the sewing ring and the stent.

16. The method of claim 14, further comprising controlling the movements of the sewing machine component and workpiece handling component using a processor which indexes the prosthetic heart valve support structure prior to every stitch.

17. The method of claim 16, wherein said controlling step further comprises placing each stitch accurately to within a tolerance of 0.002 inches (0.051 mm).

18. The method of claim 14, wherein the step of automatically monitoring comprises directing a monitoring laser toward a bobbin of the sewing machine to monitor the passage of a needle thread thereover.

19. The method of claim 14, further including automatically repeating an unsuccessful stitch.

* * * * *